(12) United States Patent
Bojarski et al.

(10) Patent No.: US 6,746,483 B1
(45) Date of Patent: Jun. 8, 2004

(54) SHEATHS FOR IMPLANTABLE FIXATION DEVICES

(75) Inventors: Ray Bojarski, Attleboro, MA (US); Paul Alexander Torrie, Marblehead, MA (US); Fraser Harvie, East Kilbride (GB); Steven Ek, Bolton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/526,960

(22) Filed: Mar. 16, 2000

(51) Int. Cl.$^7$ .................................................. A61F 2/08
(52) U.S. Cl. ................................. 623/13.14; 623/13.15
(58) Field of Search ............................. 623/13.11–13.2

(56) References Cited

U.S. PATENT DOCUMENTS

| | | | | |
|---|---|---|---|---|
| 3,921,496 A | * | 11/1975 | Helderman | 411/17 |
| 4,605,414 A | * | 8/1986 | Czajka | 623/13 |
| 5,084,050 A | | 1/1992 | Draenert | 606/77 |
| 5,139,520 A | | 8/1992 | Rosenberg | 623/13 |
| 5,383,878 A | * | 1/1995 | Roger et al. | 606/73 |
| 5,439,684 A | | 8/1995 | Prewett et al. | 424/422 |
| 5,456,274 A | * | 10/1995 | Selbee et al. | 132/275 |
| 5,490,750 A | | 2/1996 | Gundy | 411/55 |
| 5,632,748 A | | 5/1997 | Beck, Jr. et al. | 606/89 |
| 5,641,256 A | | 6/1997 | Gundy | 411/55 |
| 5,683,419 A | | 11/1997 | Thal | |
| 5,713,904 A | | 2/1998 | Errico et al. | 606/73 |
| 5,716,359 A | | 2/1998 | Ojima et al. | 606/76 |
| 5,720,765 A | | 2/1998 | Thal | |
| 5,769,894 A | | 6/1998 | Ferragamo | 623/13 |
| 5,899,938 A | | 5/1999 | Sklar et al. | 623/13 |
| 5,935,129 A | * | 8/1999 | McDevitt et al. | 606/72 |
| 5,984,926 A | * | 11/1999 | Jones | 606/72 |
| 6,203,572 B1 | | 3/2001 | Johnson | |

FOREIGN PATENT DOCUMENTS

| | | | |
|---|---|---|---|
| EP | 0 893 109 | 1/1999 | |
| FR | 2714817 | 7/1995 | |
| JP | 10014936 A | * 1/1998 | ........... A61B/17/58 |
| WO | 98/22047 | 5/1998 | |
| WO | WO 98 37835 | 9/1998 | |
| WO | 99/01084 | 1/1999 | |

OTHER PUBLICATIONS

Pontier International "Scrunchies 1" Sep. 2, 1999 http://web.archive.org/web/19990902125904/www.gifts-pontier.com/scrunch1.htm.*

Pinczewski et al., "Case Report—Integration of Hamstring Tendon Graft With Bone in Reconstruction of the Anterior Cruciate Ligament," Arthroscopy: The Journal of Arthroscopic and Related Surgery, vol. 13, No. 5, pp. 641–643 (Oct. 1997).

Innovasive Devices Website, BioROC EZ Bioabsorbable Suture Fastener, http://www.orthoindustry.com/biorocez.htm (no date).

Innovasive Devices Product Brochure, Intrafix ACL Tibial Fastener (no date).

Copy of International Search Report for International Application No. PCT/US 01/08124, mailed Oct. 29, 2001.

* cited by examiner

Primary Examiner—Corrine McDermott
Assistant Examiner—Thomas Barrett
(74) Attorney, Agent, or Firm—Fish & Richardson P.C.

(57) ABSTRACT

Sheaths for implantable fixation devices have a flexible body with a perforated wall, and an interior of the body is sized and shaped to receive the fixation device. Sheaths include a plurality of flexible or inflexible tubes arranged to form a ring, where the central cavity defined by the ring is sized and shaped to receive the fixation device.

34 Claims, 10 Drawing Sheets

SHEATHS FOR IMPLANTABLE FIXATION DEVICES

BACKGROUND OF THE INVENTION

The invention relates to devices that fix soft tissue to support structures, particularly devices that fix soft tissue grafts within bone tunnels.

In certain types of surgical procedures, soft tissue grafts must be fixed within a bone tunnel. For example, in anterior cruciate ligament (ACL) replacement surgery, a ligament graft is harvested from the patient or from a donor, and implanted within the knee by securing one end within a bone tunnel drilled through the tibia, and the other end within a bone tunnel drilled through the femur. Several ACL reconstructive techniques are described in Rosenberg, U.S. Pat. No. 5,139,520, which is incorporated herein by reference.

Referring to FIG. 1, a ligament graft 10 can be fixed within a bone tunnel using a bone screw 12. Graft 10 is made from e.g., a single or double long strip of soft tissue. To implant graft 10, the middle of the strip (not shown) is first passed in a distal direction through a first tunnel 14 in the tibia into a second tunnel 18 in the femur, and then attached to the femur tunnel (or attached to bone adjacent the femur tunnel) with a femur fixation device (not shown). Two approximately equal length segments 19a, 19b of the graft extend proximally from the attached middle portion through tunnels 18 and 14. The two ends 20a, 20b of segments 19a, 19b terminate proximal to tibial tunnel 14. Segments 19a and 19b of the graft are then fixed within tibial tunnel 14 by inserting bone screw 12 between the two segments, such that shaft 22 of the screw presses the segments against internal wall 24 of tunnel 14.

In attaching soft tissue within a bone tunnel using a bone screw, it is important that the tissue be rigidly fixed within the tunnel to prevent slippage. When the bone involved is relatively soft (less calcified), a common problem in elderly patients, screws may not adequately fix the graft to the bone.

SUMMARY OF THE INVENTION

In general, in one aspect, the invention features a sheath for an implantable fixation device. The sheath has a flexible body with a relieved wall, and the body defines an interior sized and shaped to receive the fixation device.

Embodiments of this aspect of the invention may include one or more of the following features.

The body defines a tube that is sized and shaped to receive the fixation device. For example, the device is sized and shaped to snugly receive a shaft of a bone screw, and the device's body is conformable to the bone screw shaft. Alternatively, the interior can be sized and shaped to receive both the shaft of a bone screw and a soft tissue graft.

The body includes two open, generally circular ends, or an open end and a closed end. An external loop is attached to the exterior of the body.

Rather than a single tube, the body can include a second tube attached to the first tube, the second tube being sized and shaped to receive a portion of a soft tissue graft. Alternatively, the body can include a plurality of generally parallel tubes arranged to form a ring, at least some of the tubes being sized and shaped to receive a portion of the soft tissue graft. The ring defines a central cavity between the tubes that is sized and shaped to receive the fixation device.

The body is made from a bioabsorbable material, such as hydroxyapatite, polylactic acid, or polylactic and glycolic acid, and the body is integrally formed.

The body's wall is perforated, e.g., the wall defines a plurality of holes therethrough. For example, the body is made from strands woven into a mesh structure, and the holes are the spaces between the mesh strands. A major portion of the wall is open. The wall's thickness is less than about 0.3 mm, and its exterior surface is roughened.

The device further includes a therapeutic agent in contact with the body, such as an osteoinductive agent or a growth factor. The agent is, e.g., disposed on at least a portion of an exterior surface of the body, or integrated into a material that forms the body.

The sheath can also include a washer attached to a proximal end of the body. An upper surface of the washer has a plurality of teeth for gripping bone.

In another aspect, the invention features a combination of the sheath and a fixation device.

Embodiments of this aspect of the invention may include one or more of the following features.

The fixation device is a bone screw that has a shaft sized and shaped to fit within (e.g., snugly within) the interior of the sheath. The screw's threads are rounded.

In another aspect, the invention features a sheath for an implantable fixation device that includes at least three generally parallel tubes arranged to form a ring. The ring defines a central cavity between the tubes that is sized and shaped to receive the fixation device.

Embodiments of this aspect of the invention may include one or more of the following features.

The central cavity includes a bore that is coextensive with the tubes. The ring of tubes includes, e.g., 3, 4, 5, 6, 7, or 8 tubes, and the sheath includes an external sleeve that surrounds the tubes. The tubes are flexible, and at least some of the tubes are sized and shaped to receive a portion of the soft tissue graft. At least some of the tubes are perforated. For example, in one embodiment, all the tubes have a mesh structure, and the ring of tubes is integrally formed.

In another aspect, the invention features a method of fixing soft tissue within a bone tunnel. The method includes: (a) placing both the soft tissue and a flexible, relieved, tube-shaped sheath within the bone tunnel, such that the sheath at least partly surrounds the soft tissue; and (b) positioning a fixation device within the sheath to press the soft tissue against an interior wall of the sheath, and to press the sheath against a wall of the bone tunnel, thereby fixing the soft tissue within the bone tunnel.

Embodiments of this aspect of the invention may include one or more of the following features.

The placing step includes first passing the soft tissue through the sheath, and then inserting the sheath into the bone tunnel. Alternatively, the placing step includes first inserting the sheath into the bone tunnel, and then locating the soft tissue within the bone tunnel such that the soft tissue passes through the sheath. The sheath's body has a mesh structure, and a therapeutic agent is in contact with the body.

The fixation device is a bone screw that has a shaft, and the positioning step includes positioning the shaft within the sheath. The soft tissue is a ligament graft.

In another aspect, the positioning step of the method includes positioning a fixation device within the bone tunnel adjacent an exterior surface of the sheath to compress the soft tissue within the sheath and to press the exterior surface of the sheath against a wall of the bone tunnel, thereby fixing the soft tissue within the bone tunnel.

In another aspect, the invention features a method of fixing soft tissue within a bone tunnel that includes: (a)

placing the soft tissue within the bone tunnel; (b) positioning a fixation device within an interior of a flexible, relieved, tube-shaped sheath; and (c) inserting the fixation device and the sheath into the bone tunnel to compress the soft tissue between an exterior surface of the sheath and a wall of the bone tunnel, thereby is fixing the soft tissue within the bone tunnel.

In another aspect, the invention features a method of fixing soft tissue within a bone tunnel that includes: (a) placing the soft tissue within the bone tunnel; (b) positioning a flexible, relieved, tube-shaped sheath within the bone tunnel adjacent the soft tissue; and (c) inserting a fixation device into an interior of the sheath to compress the soft tissue between an exterior surface of the sheath and a wall of the bone tunnel, thereby fixing the soft tissue within the bone tunnel.

In another aspect, the invention features a method of fixing soft tissue within a bone tunnel that includes: (a) inserting a sheath into the bone tunnel, the sheath having at least three generally parallel tubes arranged to form a ring, the ring defining a central cavity between the tubes; (b) passing segments of the soft tissue through at least two of the tubes; and (c) positioning a fixation device within the central cavity of the ring to compress the tubes between the fixation device and a wall of the bone tunnel, and to compress the soft tissue segments within their respective tubes, thereby fixing the soft tissue within the bone tunnel.

Embodiments of this aspect of the invention may include one or more of the following features.

The passing step is performed prior to inserting the sheath into the bone tunnel. The sheath has exactly four tubes arranged to form the ring, and the passing step includes passing segments of the soft tissue through each of the four tubes. The fixation device is a bone screw having a shaft, and the positioning step includes positioning the shaft within the central portion of the ring.

In another aspect, the invention features a method of fixing soft tissue within a bone tunnel that includes: (a) inserting a sheath into the bone tunnel, the sheath having two generally parallel tubes; (b) passing a portion of the soft tissue through a first of the two tubes; and (c) positioning a fixation device within the second of the two tubes to compress the first tube between the fixation device and a wall of the bone tunnel, and to compress the portion of the soft tissue within the first tube, thereby fixing the soft tissue within the bone tunnel.

The invention may include one or more of the following advantages.

The flexibility and thinness of certain embodiments of the sheath allows the sheath to conform, e.g., to the shape of the fixation device, or to the shape of a bone tunnel.

In certain embodiments, the sheath protects the soft tissue graft from laceration or cutting by threads of a fixation screw, and reduces twisting of the graft upon insertion of a screw.

The relief in the sheath, e.g., perforations in a wall of the sheath, allows in situ contact between a soft tissue graft and the wall of a bone tunnel, promoting development of Sharpy-like fibers and permanent attachment of the soft tissue to the bone.

Therapeutic agents, such as osteoinductors or growth factors, can be disposed on or embedded into the material of the sheath, allowing delivery of the agent directly to the site of fixation.

Other embodiments and advantages of the invention will be apparent from the following description and from the claims.

DESCRIPTION OF THE PREFERRED EMBODIMENTS

Embodiments of the invention feature sheaths that surround bone screws and soft tissue grafts to improve fixation of the grafts. In its simplest form, the sheath is a flexible, mesh tube that surrounds only the bone screw, both the bone screw and the graft, or only the graft. In other embodiments, the sheath includes multiple tubes.

Figure 1:
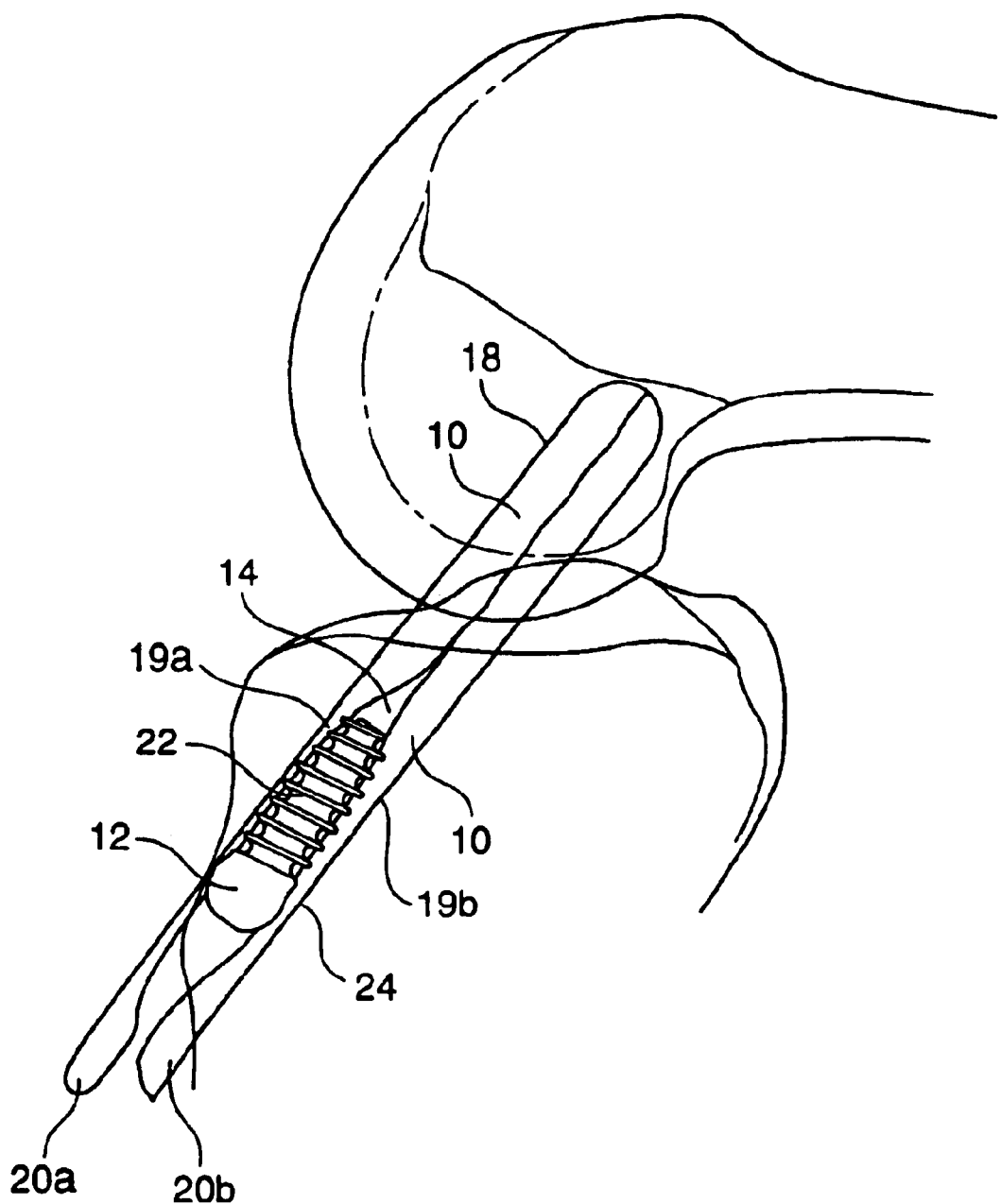
FIG. 1 is a sectional view of a prior art technique of fixing a ligament graft within a tibial bone tunnel by using a bone screw.
Figure 2A:
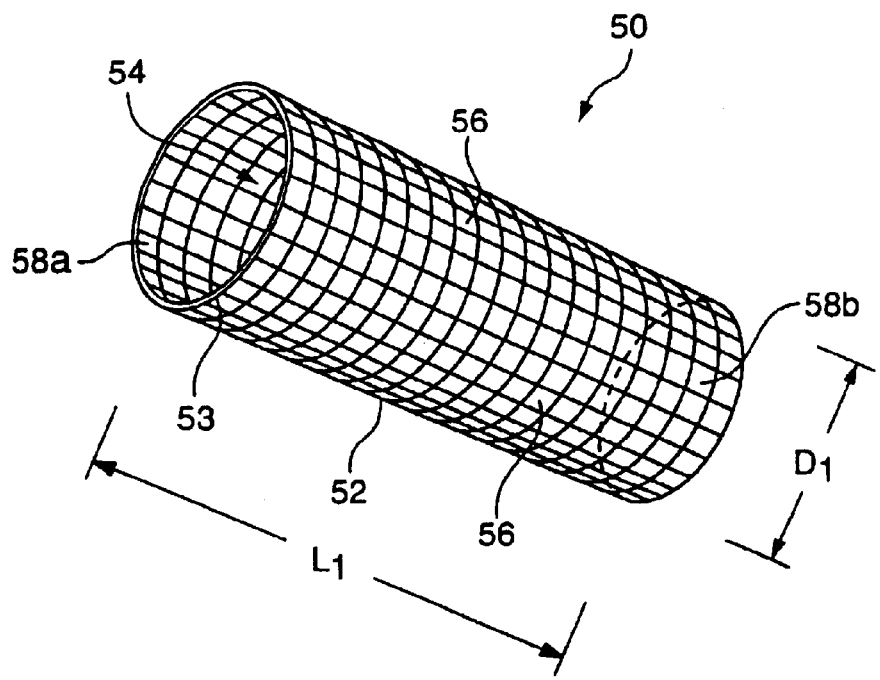
FIG. 2A is a perspective view of a bone screw sheath.
Figure 2B:
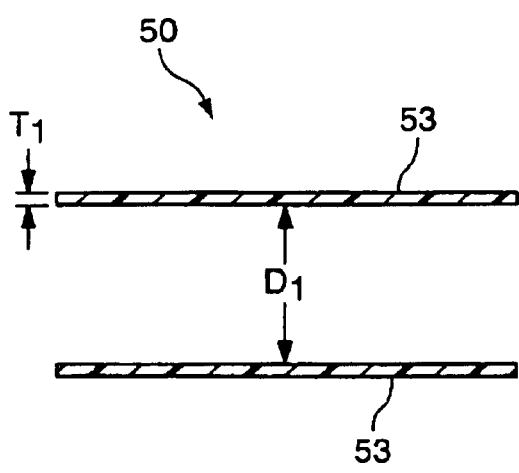
FIG. 2B is a sectional view of the bone screw sheath of FIG. 2A.
Figure 2C:
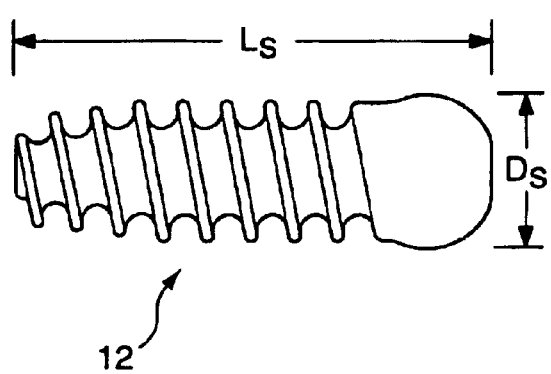
FIG. 2C is a sectional view of the bone screw of FIG. 1.

Referring to FIGS. 2A–2C, a sheath 50 has a tube-shaped body 52 that defines a generally cylindrical exterior surface 53 and a generally cylindrical interior 54. Body 52 is formed from a biocompatible material woven into a mesh structure. The mesh defines numerous holes 56 that expose interior 54 to the outside. Sheath 50 also has two circular, open ends 58a, 58b, allowing a tissue graft to pass entirely through the interior of the sheath.

Interior 54 of sheath 50 is sized and shaped to receive bone screw 12. Sheath 50 has an internal diameter $D_1$ greater than the diameter $D_s$ of bone screw 12, so that both screw 12 and segments 19a and 19b of graft 10 can fit snugly within the sheath. The sheath has a length $L_1$ slightly larger than the length $L_s$ of screw 12. The mesh body 52 is thin and flexible, allowing the sheath to adjust to snugly surround the screw; body 52 can be compressed to reduce the volume of interior 54, twisted, or stretched. Since sheath 50 is thin and flexible rather than rigid, it cannot on its own shore up soft bone, or fix a graft within a bone tunnel. (I.e., sheath 50 is not designed to be used alone as a fixation device or as a solid, rigid reinforcement of soft bone.)

In some embodiments, the threads forming the mesh body 52 are larger in the radial direction than in the axial direction. This difference in thread size results in sheath 50 being less flexible radially than axially. In these embodiments, the diameter $D_1$ is more resistant to expansion or contraction than length $L_1$. In other embodiments, the thread size is equal throughout body 52.

Diameter $D_1$ is, e.g., between about 8 and 10 mm, and $L_1$ is, between about 25 and 40 mm. If sheath 50 is designed for a 7×25 bone screw (7 mm diameter, 25 mm length), then $L_1$ is, e.g., about 30 mm, and $D_1$ is, e.g., about 9 mm. Most of exterior surface 53 is open. For example, about 40% of the area exterior surface 53 is mesh strands, and about 60% is holes 56. The thickness $T_1$ the mesh wall of sheath 50 is, for example, less than about 0.3 mm, e.g., about 0.1–0.2 mm.

Body 52 can be made from a variety of bioabsorbable materials, including polylactic acid, or polylactic glycolic acid. Alternatively, body 52 can be made from a blend of absorbable materials, or from a non-absorbable material, such as a polyester. The material forming the body preferably has a higher coefficient of friction than graft 10, so that exterior surface 53 of the sheath grips internal wall 24 of bone tunnel 14 more firmly than graft 10 alone, improving fixation.

Body 52 can be formed, e.g., by weaving, braiding, knitting, or crocheting strands of the material to form the cylindrical shape, or by extrusion, using techniques known in the art. The strands forming body 52 have diameters of about 0.1–1.0 mm, e.g., 0.4–0.6 mm, or 0.51 mm.

Although sheath 50 can be used with a variety of fixation screws, screw 12 preferably has blunt or rounded screw threads, as opposed to sharp threads, so that the threads do not cut the sheath or the soft tissue graft. A typical rounded-thread screw is shown in Roger et al., U.S. Pat. No. 5,383,878, which is incorporated herein by reference.

Figure 3:
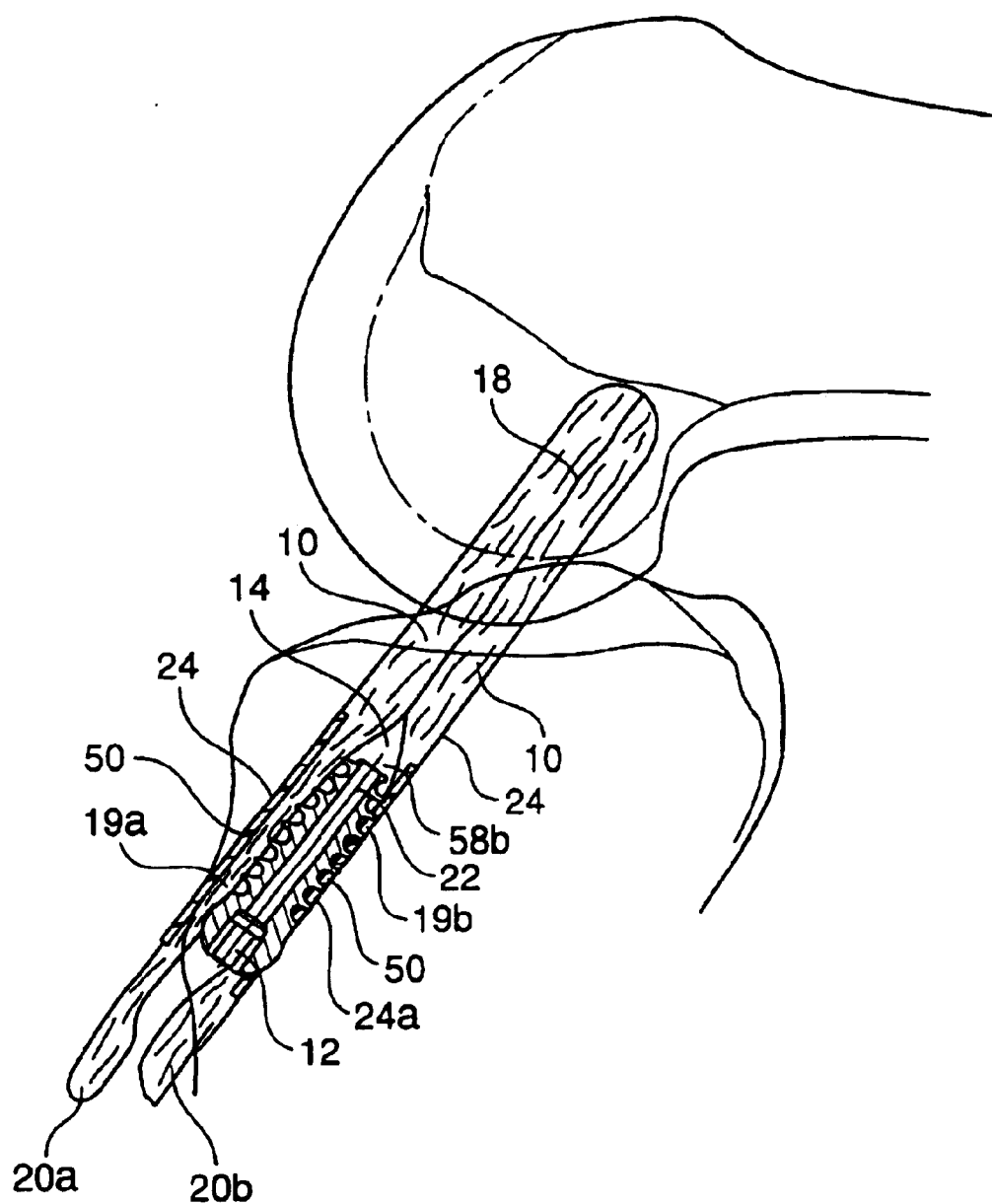
FIG. 3 is a sectional view of a the bone screw and sheath of FIGS. 2A–2C fixing a ligament graft within a bone tunnel in the tibia.

Referring to FIG. 3, in operation, a surgeon first forms bone tunnels 14 and 18 within the tibia and femur, respectively. Next, graft 10 is fixed to the femur tunnel using any technique known in the art (not shown). For example, the femur fixation device can include a loop attached to the femur at a distal end of femur tunnel 18. End 20a of the graft is passed distally through tunnels 14 and 18, passed through the loop, and then pulled proximally through tunnels 18 and 14 until the middle portion of the graft is centered on the loop. Alternatively, the graft can be threaded through the loop prior to implantation of the loop. In addition, rather than using a loop, one end of graft 10 can be fixed within the femur tunnel, allowing the other end to extend proximally through tunnels 18 and 14. To increase the number of segments available for fixation, multiple strips of soft tissue (i.e., multiple grafts) can be separately attached to the femur. Various techniques for attaching a graft within a bone tunnel are described in Ferragamo, U.S. Pat. No. 5,769,894, which is incorporated herein by reference, and in Rosenberg, supra.

After attaching graft 10 within (or adjacent to) femur tunnel 18, the surgeon passes ends 20a, 20b of graft 10 through interior 54 of sheath 50 (via open ends 58a and 58b), and then slides sheath 50 into tibial tunnel 14. The diameter of tunnel 14 is only slightly larger than the outer diameter of sheath 50, such that sheath 50 fits snugly within tunnel 14. Alternatively, sheath 50 can be inserted into tunnel 14 prior to passing the graft through the sheath. To insert sheath 50 into tibial tunnel 14, the surgeon can use a delivery tool, such as a rigid tube detachably fixed to the distal end of the sheath. Alternatively, a suture can be threaded through the distal end of sheath 50, and the sheath can be pulled into place within tunnel 14 using the suture.

The surgeon then inserts bone screw 12 into interior 54 of sheath 50, between segments 19a and 19b of the graft. The screw may be inserted using an insertion tool known in the art, such as a screw driver. When screw 12 is in place as shown in FIG. 3, the screw presses segments 19a and 19b of the graft against the interior surface of sheath 50, and presses exterior surface 53 of the sheath against wall 24, fixing the graft within the tunnel.

As shown in FIG. 3, when screw 12 is inserted, it will typically be slightly off center, such that the screw's threads dig into wall 24 of bone tunnel 14 along a segment 24a of wall 24. For example, if screw 12 has a major diameter of 9 mm, and a minor diameter of 7 mm, then the screw threads will dig into wall 24 by about 1 mm along segment 24a, where segment 24a is about 120 degrees. This engagement of the threads with segment 24a of the wall helps hold screw 12 within tunnel 14, and therefore improves fixation of graft 10 within the tunnel.

The presence of sheath 50 within bone tunnel 14 improves fixation of graft 10. Since exterior surface 53 of sheath 50 has a higher coefficient of friction than graft 10, sheath 50 is less likely than graft 10 (which is made of tissue) to slide along wall 24 of the tunnel, or to twist when screw 12 is inserted into the tunnel. In addition, since body 52 of sheath 50 has a mesh structure, portions of graft 10 protrude through holes 56 of the mesh, resisting sliding of graft 10 relative to sheath 50. The flexibility of sheath 50 allows the sheath to conform to the shape of wall 24, maximizing the surface area contact between the exterior surface of the sheath and wall 24, thereby increasing frictional forces between the sheath and the wall.

After screw 12 has been inserted into tunnel 14, the surgeon may trim the portions of segments 19a and 19b that extrude proximally from tunnel 14, completing the surgical procedure. Over time, graft 10 permanently affixes to wall 24 by growth of Sharpy-like fibers between the soft tissue of graft 10 and the bone tissue of wall 24. ("Sharpy-like fibers" are collagenous fibers that grow from bone into a soft tissue graft. The presence of Sharpy-like fibers indicate good bony growth to the graft, and therefore good fixation. See Pinczewski et al., "Integration of Hamstring Tendon Graft With Bone in Reconstruction of the Anterior Cruciate Ligament," *Arthroscopy*, 13: 641–43 (1997). The open holes 56 in body 52 of the sheath facilitate permanent fixation by increasing the direct contact between the graft and the bone tunnel wall. Sheath 50 eventually dissolves, and new bone grows to fill its position.

To accelerate bone growth and permanent attachment of graft 10 to wall 24, sheath 50 can include an osteoinductive agent, such as hydroxyapatite, tricalcium phosphate, calcium sulphate, or a "ceramic" (a calcium and potassium crystalline). The osteoinductive agent can be applied to sheath 50 prior to surgery by, e.g., spraying the sheath with the agent, by dipping the sheath into a bath that includes the agent, by dusting or spraying the agent onto the sheath, or by filling the sheath with a gel that includes the agent. In addition, the strands of material forming the mesh body 52 can be hollow, and the agent can be within the hollow interiors of the strands. Alternatively, the agent can be incorporated into the material that forms body 52. For example, the agent can be blended into the material used to make the threads that form mesh body 52, or can be added to the fibers as an osteoinductive felt.

Other therapeutic agents, such as growth factors (e.g., tissue growth factor or platelet derived growth factor), bone morphogenic proteins, stem cells, osteoblasts, and cytokines, can also be included in the sheath. These bioactive agents can be added using the techniques described above, or can be blended into the material that forms body 52 using micro-encapsulation or nanoparticles. For example, body 52 can be formed from a material comprising microspheres of the agent and a polymer, such as polylactic glycolic acid. The microspheres of the agent and polymer can be prepared using known techniques. See, e.g., Cohen et al., "Controlled Delivery Systems for Proteins Based on Poly(Lactic/Glycolic Acid) Microspheres," *Pharm. Research*, 8:713–20 (1991); DeLuca et al., U.S. Pat. Nos. 5,160,745 and 4,741,872. Rather than forming microspheres, the agent and polymer can also be mixed together using, e.g., sintering techniques. See, Cohen et al., "Sintering Techniques for the Preparation of Polymer Matrices for the Controlled Release of Macromolecules," *J. Pharm. Sciences*, 73:1034–37 (1984). The bioactive agents can also be attached to body 52 using adhesives or electrical charge, or can be directly loaded onto the sheath by a delivery mechanism after implantation of the sheath.

Figure 4:
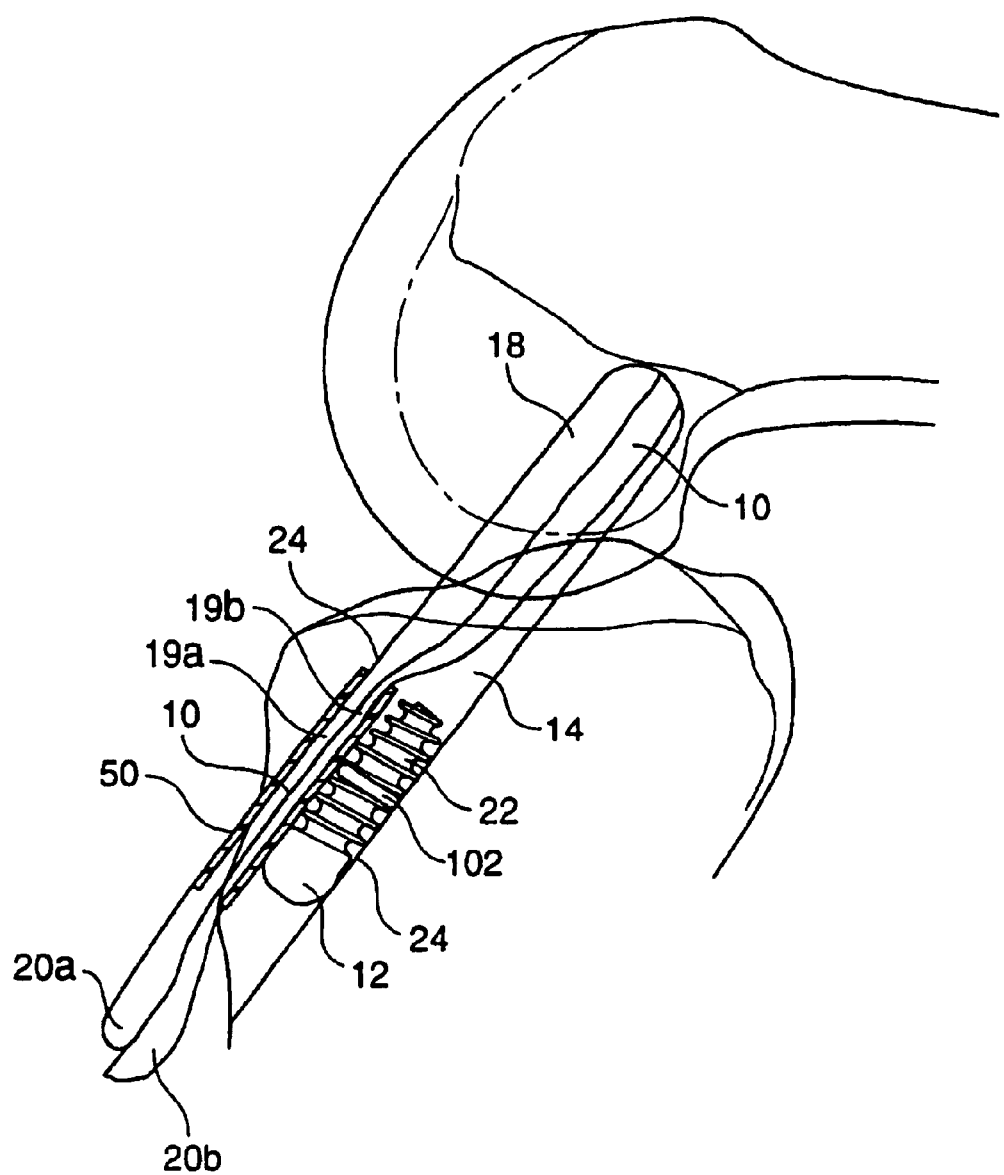
FIGS. 4 and 5 are sectional views illustrating alternative arrangements for the bone screw, sheath, and graft of FIG. 3 within the bone tunnel in the tibia.

Other embodiments are within the scope of the claims. For example, the sheath can be used to assist fixation of a bone screw within the femur tunnel 18, in addition to the tibial tunnel 14. Referring to FIG. 4, screw 12 can be placed between sheath 50 and wall 24 of tunnel 14. In this embodiment, rather than inserting screw 12 into the sheath after placement of the sheath within tunnel 14, screw 12 is inserted into tunnel 14 along the side of the sheath. To hold screw 12 to the side of the sheath, the sheath can optionally include an external loop 102. Loop 102 has a diameter slightly larger than the diameter of screw 12, so that shaft 22 of screw 12 fits snugly within the loop. Loop 102 can be made from the same material as body 52, or can be made from an inflexible, rigid material.

When screw 12 is inserted, it compresses graft 10 within the sheath, and presses exterior surface 53 of the sheath against wall 24, fixing graft 10 within tunnel 14.

Figure 5:
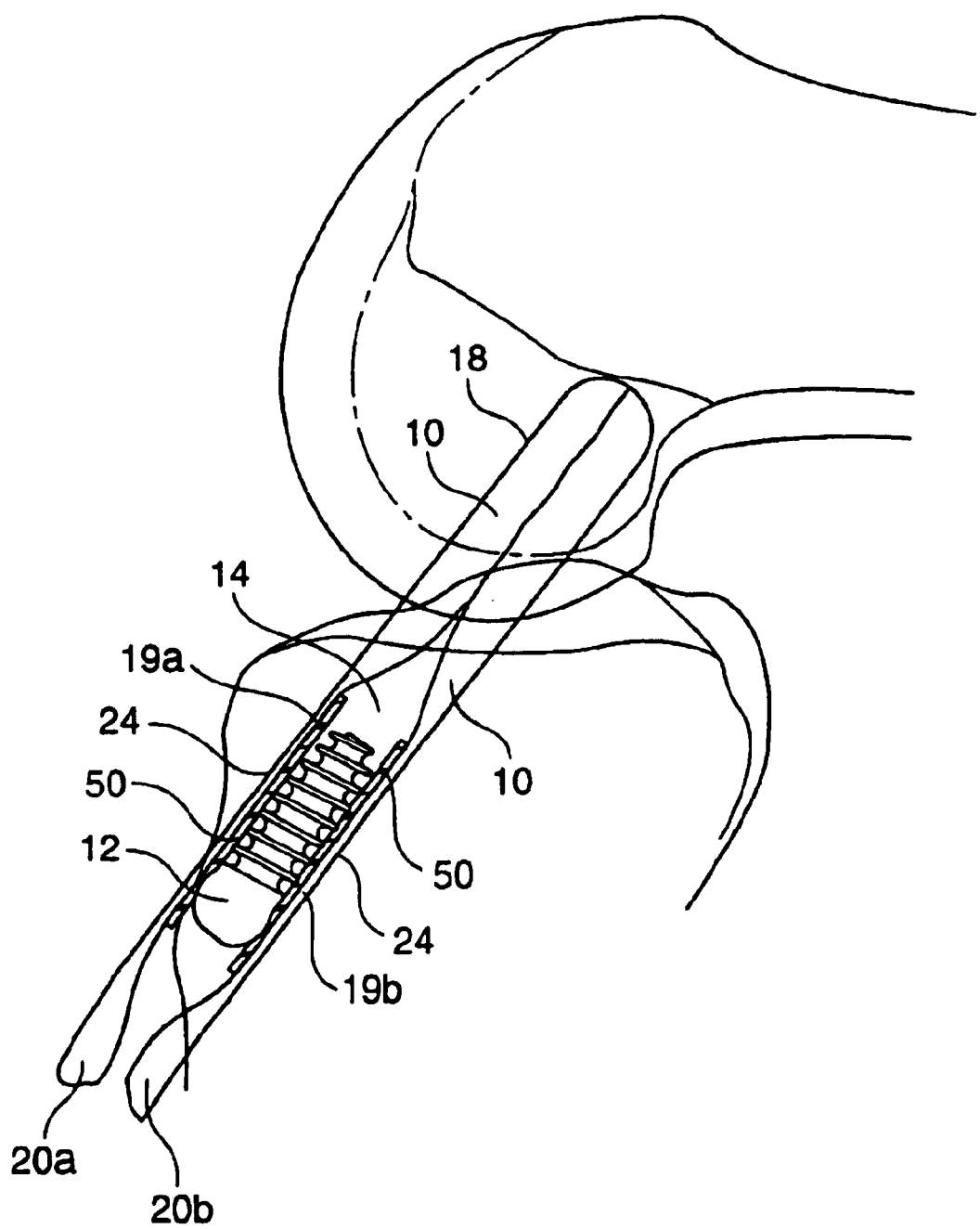

Referring to FIG. 5, segments 19a and 19b of graft 10 can be positioned radially outside of sheath 50. In this embodiment, when sheath 50 is inserted into tunnel 14, it is located between ends 19a and 19b of the graft, so that the graft surrounds the sheath, rather than the sheath surrounding the graft. Screw 12 is then inserted into the sheath, pressing segments 19a and 19b between exterior surface 53 of the sheath and wall 24, fixing the graph in place. Alternatively, the screw can first be inserted into the sheath, and then the sheath and screw together can be positioned within the bone tunnel.

The structure of the bone screw sheath can be modified as well. The diameter $D_1$, length $L_1$, and thickness T of the sheath can be varied to accommodate different sized bone tunnels, different sized screws, and different deployment methods. For example, in the deployment method of FIG. 5, the inner diameter $D_1$ of the sheath can be approximately equal to the diameter $D_s$ of the screw shaft, so that the screw fits very snugly within the sheath, and exterior surface 53 of the sheath conforms to the shape of the screw shaft.

In the deployment methods shown in FIGS. 4 and 5, the sheath need not be more rigid in the radial direction than in the axial direction. The threads forming the mesh body, therefore, are generally the same size in both the radial and axial directions. In addition, sheaths used in the deployment method of FIG. 5 can have less open space than sheaths used with the method of FIGS. 3 or 4. (I.e., less than 60% of the sheath's surface area will be holes.)

If the bone is particularly soft, sheath 50 can be woven tighter, so that the sheath is less flexible, thereby providing a more firm substrate for screw 12 to engage.

The sheath need not have a mesh structure. For example, the sheath can have a solid body with holes cut through the body, allowing communication between the exterior and interior of the sheath. In addition, the sheath's body need not be integrally formed. For example, the body can be formed by winding a strip of material around an implantable device to form a relieved body that defines an interior.

The sheath can have relief structures other than holes to allow communication between the exterior and interior. For example, other types of perforations, such as slits, can be used, instead of holes. In addition, the device can have a solid wall with thinned sections. When implanted, the thinned sections biodegrade more quickly than other sections of the wall, such that in situ, the device develops perforations.

To increase the coefficient of friction of exterior surface 53 to improve fixation of the sheath within the bone tunnel, exterior surface 53 can have a roughened finish.

Figure 6:
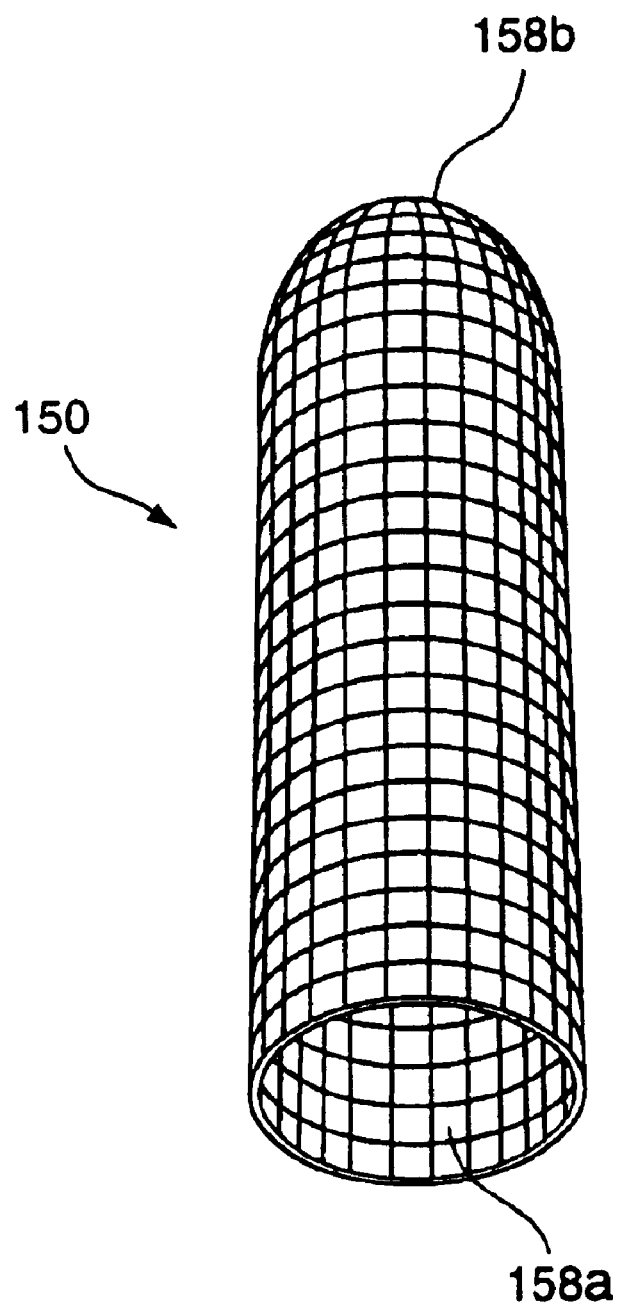
FIG. 6 is a perspective view of an alternative embodiment of the sheath of FIG. 2A.

Referring to FIG. 6, rather than having two open circular ends, sheath 150 has an open end 158a and a closed end 158b. Closed end 158b gives sheath a "bag" or "sock" shaped structure.

Figure 7A:
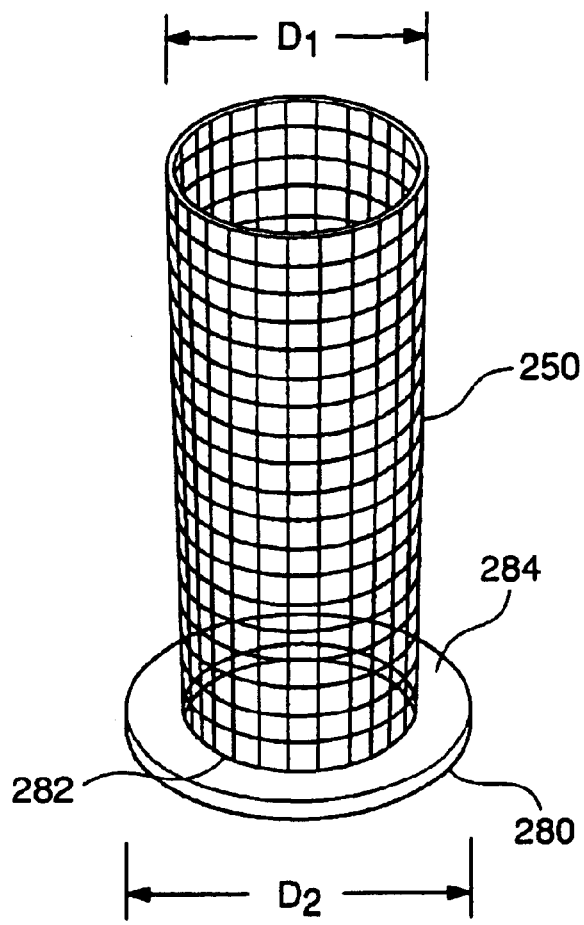
FIG. 7A is a perspective view of an alternative embodiment of the sheath of FIG. 2A that includes a washer.
Figure 7B:
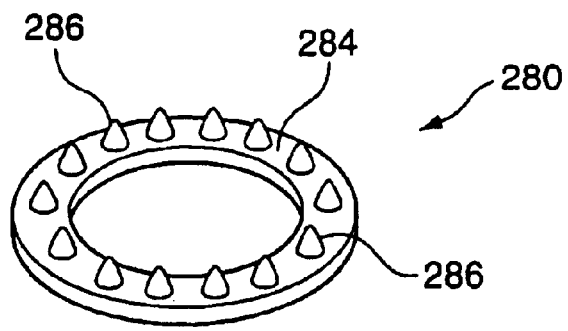
FIG. 7B is a top view of the washer of FIG. 7A.

Referring to FIG. 7A, a sheath 250 includes a washer 280 attached to the proximal end 282 of the sheath. The washer 280 has a diameter $D_2$ that is larger than diameter $D_1$ of sheath 250, and is larger than the diameter of the bone tunnel. Washer 280 prevents proximal end 282 of the sheath from passing into the bone tunnel when the screw is inserted into the sheath, thereby ensuring that the sheath is ultimately positioned around the screw shaft, rather than in front of the screw. Rather than being circular, the washer can be square, triangular, or any other shape, so long as it has a dimension larger than the diameter of the bone tunnel. Referring to FIG. 7B, the upper surface 284 of the washer can include teeth or spikes 286 to grip bone, thereby reducing twisting of sheath 250 when a bone screw is inserted into the sheath. The washer can be made from a bioabsorbable material, or a non-absorbable, biocompatible material. In operation, the washer can be detached from the sheath after implantation of the graft and bone screw, or can be left attached to the sheath.

Figure 8:
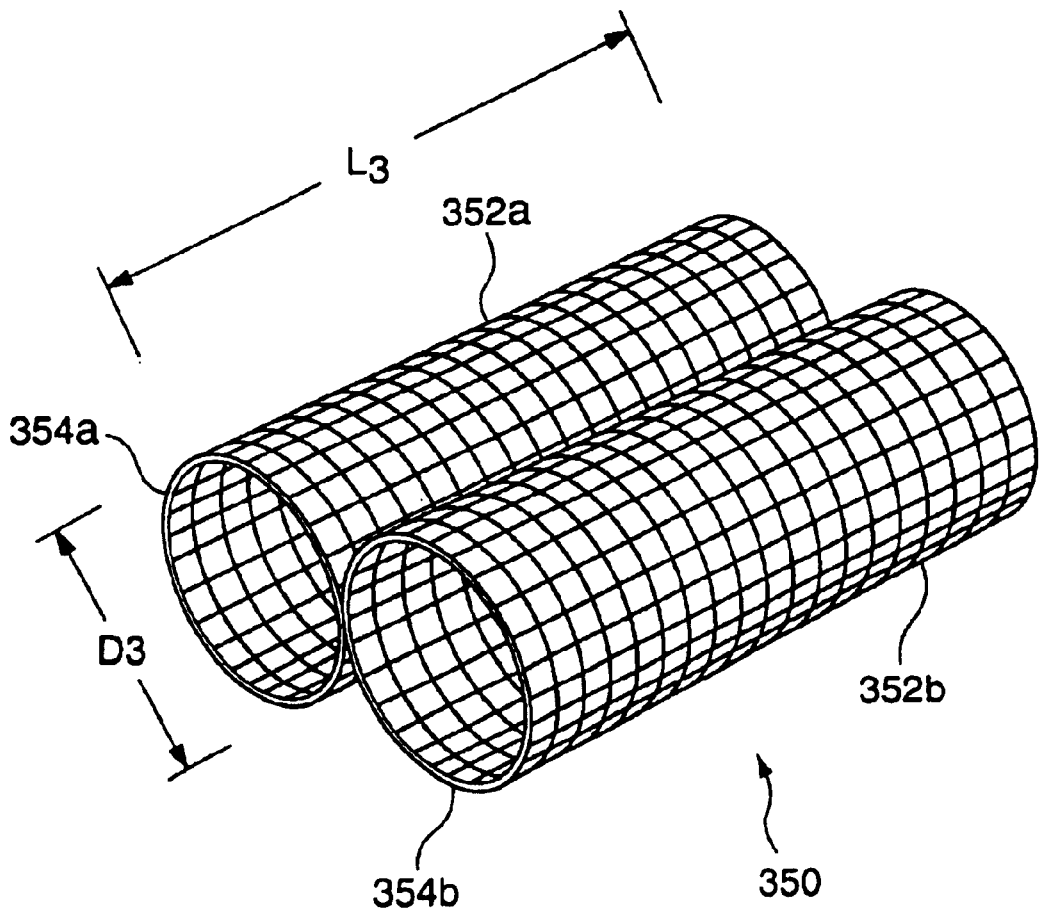
FIG. 8 is a perspective view of an alternative bone screw sheath that includes two tubes.

Referring to FIG. 8, a sheath 350 includes two contiguous, parallel mesh tubes, 352a and 352b. Tubes 352a and 352b are integrally woven, braided, knitted, or crocheted from threads. Each tube has a diameter $D_3$ that is slightly larger than diameter $D_s$ of screw 12, and slightly less than diameter $D_1$ of sheath 50. Diameter $D_3$ can be, e.g., 2 mm, 4 mm, 6 mm, or 8 mm. Sheath 50 has a length $L_3$ approximately equal to the length of a fixation screw, e.g., about 10–50 mm, or 20–35 mm. The walls 354a, 354b of tubes 352a and 352b each have a thickness of, e.g., between 0.1 mm and 1.0 mm.

In operation, a soft tissue graft is passed through one of the tubes (e.g., tube 352a), and the fixation screw is inserted into the second tube (e.g., tube 352b). When the is sheath, graft, and fixation screw are positioned within the bone tunnel, tube 352a is compressed between the screw and a wall of the bone tunnel. The graft, therefore, is compressed within tube 352a, fixing the graft within the bone tunnel.

Figure 9:
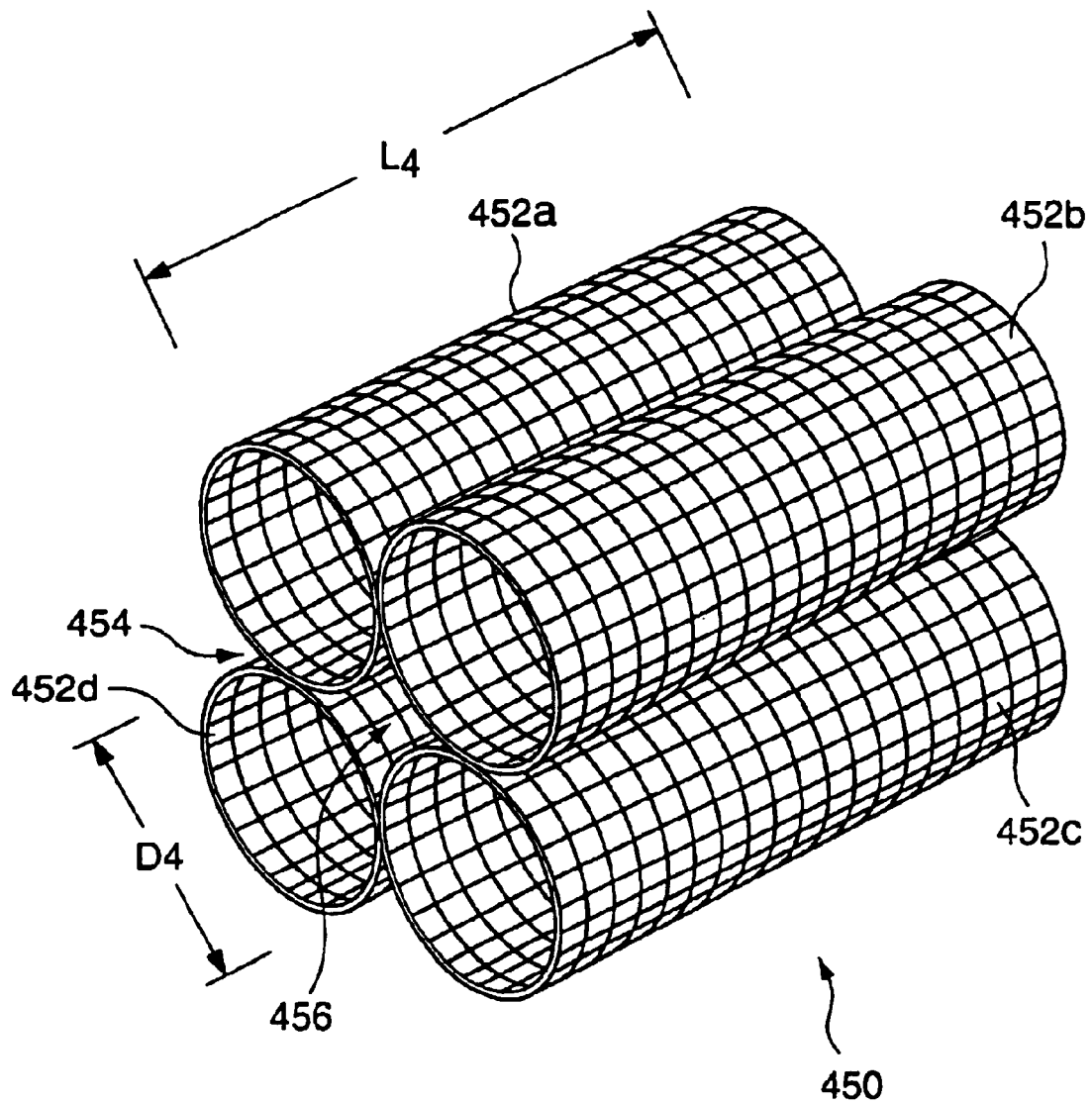
FIG. 9 is a perspective view of an alternative bone screw sheath that includes four tubes arranged to form a ring.

Referring to FIG. 9, a sheath 450 includes four parallel mesh tubes, 452a, 452b, 452c, and 452d. The four tubes are arranged to form a ring 454. Ring 454 defines a central cavity 456 disposed between the tubes. The cavity defines an axial bore that is coextensive with the axial lengths of each of the tubes.

Each tube 452a, 452b, 452c, and 452d has a diameter $D_4$ and a length $L_4$ similar to diameter $D_3$ and length $L_3$ of sheath 350 (FIG. 8). As with sheath 350, the tubes of sheath 450 are integrally woven.

In operation, segments of a soft tissue graft are passed through each of tubes 452a–452d. The surgeon can either use multiple, independent tissue grafts separately attached to the femur tunnel, or can split the proximal end of a single graft into four separate segments. The sheath is then inserted into the tibial bone tunnel, and a fixation screw is inserted into central cavity 456. When the sheath, soft tissue, and screw are in place within the bone tunnel, the tubes are compressed between the screw and the bone tunnel wall, and the soft tissue segments are compressed within each tube, thereby fixing the soft tissue within the bone tunnel.

In the embodiment shown FIG. 9, sheath 450 includes four tubes forming a ring. The sheath need not, however, be limited to this number. For example, the sheath can include a ring of 3, 5, 6, 7, or 8 tubes. In addition, soft tissue need not be passed through each tube. For example, soft tissue segments can be passed through two tubes, leaving the remaining tubes unoccupied.

Instead of being integrally woven, the tubes of sheath 450 can be woven, braided, or knitted separately, and attached together using, e.g., stitching, spot welding, or an adhesive. The tubes can also be solid rather than mesh, and need not all have the same diameter. In addition, unlike the single tube sheaths of FIGS. 2A, 6, and 7, sheath 450 can be rigid, rather than flexible.

Figure 10:
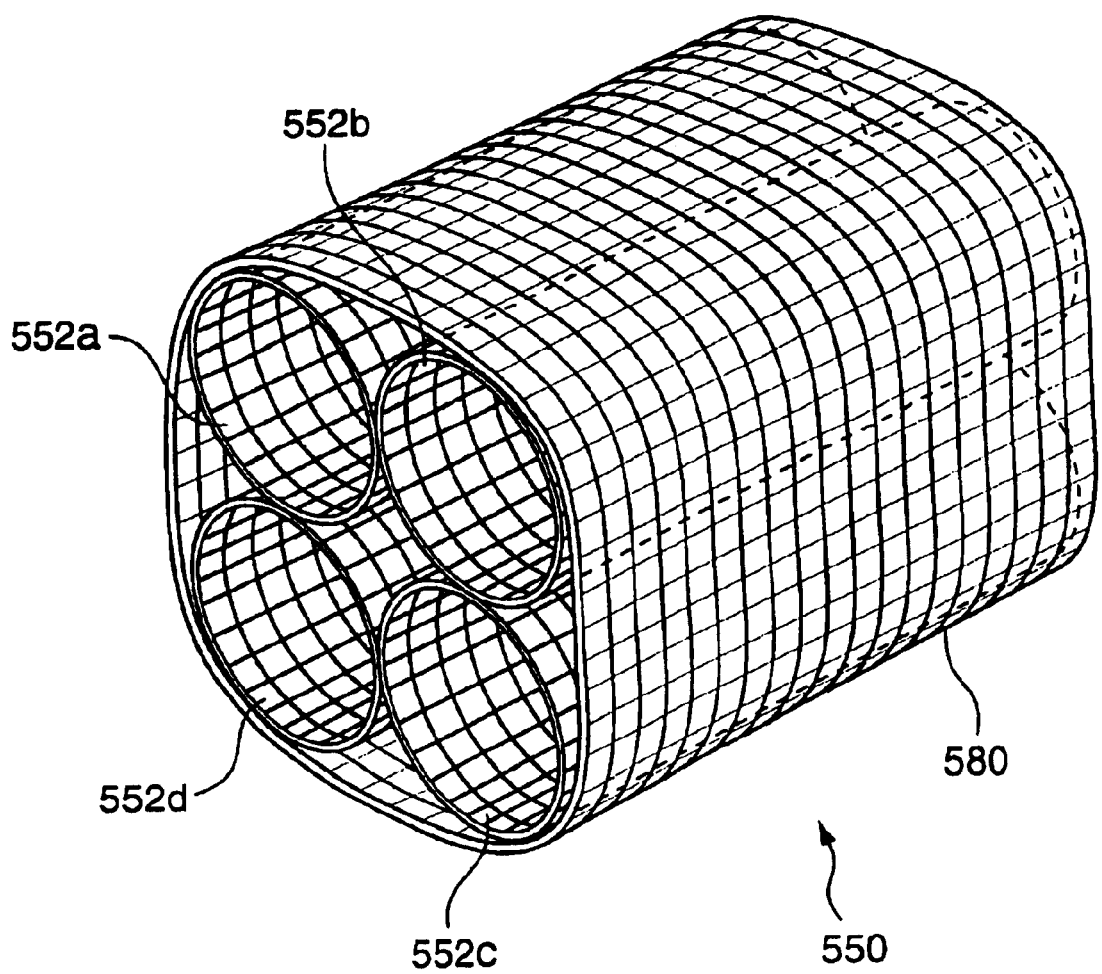
FIG. 10 is a perspective view of the bone screw sheath of FIG. 9 with an external sleeve.

Referring to FIG. 10, sheath 550 is identical to sheath 450 in all respects, except that sheath 550 further includes a mesh sleeve 580 that surrounds the four tubes 552a–552d. Sleeve 580 is axially coextensive with tubes 552a–552d, and is integrally woven with the four tubes. Alternatively, sleeve 580 can be a separate solid or mesh structure adhesively bound to the four tubes. Sleeve 580 acts to stabilize sheath 550, and facilitates insertion of the sheath into the bone tunnel. For example, to insert sheath 550, a suture or delivery tool can be attached to sleeve 580, rather than directly to one of the tubes.

The sheaths need not be used exclusively with bone screws or bone tunnels. Rather, the invention includes sheaths that improve fixation of other types of implantable fixation devices, such as soft tissue tacks, plugs, and suture anchors. The size and shapes of the sheaths can be varied to accommodate the different types of fixation devices. For example, in one embodiment, soft tissue can be positioned inside of a sheath, and the sheath can be attached to the side of a bone with a fixation device such as a tack.

What is claimed is:

1. A combination comprising:
    a sheath including a flexible body defining a tube having two ends, each end having an opening of substantially the same dimensions, the tube having a relieved wall and defining an interior sized and shaped to receive both a shaft of a bone screw and a soft tissue graft; and
    a bone screw having a shaft sized and shaped to fit within the interior of the sheath.

2. A combination comprising:
    a sheath including a flexible body defining a tube having two ends, each end having an opening of substantially the same dimensions, the tube having a perforated relieved wall defining an interior sized and shaped to receive a soft tissue fixation device that is configured to be inserted into a bone tunnel; and
    the soft tissue fixation device.

3. The sheath of claim 2, wherein the wall defines a plurality of holes therethrough.

4. The sheath of claim 3, wherein the body comprises strands that form a mesh structure, the strands defining spaces therebetween that define the holes.

5. A combination comprising:
    a sheath including a flexible body defining a tube having two ends, each end having an opening of substantially the same dimensions, the tube having a relieved wall with a major portion of the wall being open, the wall defining an interior sized and shaped to receive a soft tissue fixation device that is configured to be inserted into a bone tunnel; and
    the soft tissue fixation device.

6. A combination comprising:
    a sheath including a flexible body having a roughened exterior surface and defining a tube having two ends, each end having an opening of substantially the same dimensions, the tube having a relieved wall and defining an interior sized and shaped to receive a soft tissue fixation device that is configured to be inserted into a bone tunnel; and
    the soft tissue fixation device.

7. A combination comprising:
    a sheath including a flexible body defining a tube having two ends, each end having an opening of substantially the same dimensions, the tube having a relieved wall and defining an interior sized and shaped to receive a fixation device and a soft tissue graft; and
    the fixation device.

8. The combination of claim 7, wherein each opening is circular.

9. The combination of claim 7, wherein the body is made from a bioabsorbable material.

10. The combination of claim 7, wherein the tube comprises a biocompatible material selected from the group consisting of hydroxyapatite, polylactic acid, and polylactic glycolic acid.

11. The combination of claim 7, wherein the wall has a thickness less than about 0.3 mm.

12. The combination of claim 7, wherein the body is integrally formed.

13. The combination of claim 7, further comprising a therapeutic agent in contact with the body.

14. The combination of claim 13, wherein the therapeutic agent is an osteoinductive agent.

15. The combination of claim 13, wherein the therapeutic agent is a growth factor.

16. The combination of claim 13, wherein the therapeutic agent is disposed on at least a portion of an exterior surface of the body.

17. The sheath of claim 13, wherein the therapeutic agent is integrated into a material that forms the body.

18. The combination of claim 7, wherein the fixation device is a bone screw, the bone screw having a shaft sized and shaped to fit within the interior of the sheath.

19. The combination of claim 18, wherein the soft tissue graft and the shaft of the bone screw fits snugly within the interior of the sheath.

20. The combination of claim 18, wherein the tube is sized and shaped to snugly receive the shaft of the bone screw and the soft tissue graft.

21. The sheath of claim 20, wherein the tube is conformable to a shape of the shaft of the bone screw and the soft tissue graft.

22. A combination comprising:
    a sheath including a flexible body defining a tube having two ends, each end having an opening of substantially the same dimensions, the tube having a relieved wall and defining an interior sized and shaped to receive a bone screw; and
    a bone screw having a shaft sized and shaped to fit snugly within the interior of the sheath, the shaft including generally rounded screw threads.

23. A combination comprising:
a sheath including a flexible body having two ends, each end having an opening of substantially the same dimensions, the body having a relieved wall and defining an interior sized and shaped to receive the shaft of a bone screw, and
the bone screw having a shaft sized and shaped to fit snugly within the interior of the sheath, the shaft including generally rounded screw threads.

24. The combination of claim 23, wherein the body is conformable to a shape of the shaft of the bone screw.

25. The combination of claim 23, wherein the body is sized and shaped to receive both the shaft of the bone screw and a soft tissue graft.

26. The combination of claim 23, wherein each opening is circular.

27. The combination of claim 23, wherein the body defines a first tube and a second tube connected to the first tube, the first tube being sized and shaped to receive the shaft of the bone screw and the second tube being sized and shaped to receive a portion of a soft tissue graft.

28. The combination of claim 23, wherein the sheath includes a plurality of generally parallel tubes arranged to form a ring, a portion of each tube forming a portion of the relieved wall of the flexible body.

29. The combination of claim 28, wherein at least some of the tubes are sized and shaped to receive a portion of a soft tissue graft.

30. The combination of claim 28, wherein the ring defines a central cavity between the tubes that comprises the interior sized and shaped to receive the bone screw.

31. The combination of claim 23, wherein the relieved wall is perforated.

32. The combination of claim 31, wherein the wall defines a plurality of holes therethrough.

33. The combination of claim 32, wherein the body comprises strands that form a mesh structure, the strands defining spaces therebetween that define the holes.

34. The combination of claim 23, wherein a major portion of the wall is open.

* * * * *

UNITED STATES PATENT AND TRADEMARK OFFICE
CERTIFICATE OF CORRECTION

PATENT NO.     : 6,746,483 B1
DATED          : June 8, 2004
INVENTOR(S)    : Raymond Bojarski et al.

It is certified that error appears in the above-identified patent and that said Letters Patent is hereby corrected as shown below:

Title page,
Item [75], Inventors, "Ray Bojarski" should read -- Raymond A. Bojarski --.
Item [56], References Cited, U.S. PATENT DOCUMENTS, insert
-- 6,602,290       8/2003          Esnouf et al. --.

Column 3,
Line 6, after "thereby", delete "is".

Column 7,
Line 15, "Referring to Fig. 4" should begin a new paragraph.

Column 8,
Line 48, before "sheath", delete "is".

Column 9,
Line 48, change "graft; and" to -- graft, with the graft positioned between the shaft of the bone screw and the wall; and --.
Line 57, change "tunnel; and" to -- tunnel, and a graft, with the graft positioned between the soft tissue fixation device and the wall; and --.
Lines 59 and 61, change "sheath" to -- combination --.

Column 10,
Lines 4 and 14, change "tunnel;" to -- tunnel, and a graft, with the graft positioned between the soft tissue fixation device and the wall; --.
Line 22, change "graft;" to -- graft, with the graft positioned between the fixation device and the relieved wall; --.

UNITED STATES PATENT AND TRADEMARK OFFICE
CERTIFICATE OF CORRECTION

PATENT NO. : 6,746,483 B1
DATED : June 8, 2004
INVENTOR(S) : Raymond Bojarski et al.

It is certified that error appears in the above-identified patent and that said Letters Patent is hereby corrected as shown below:

Column 10 (cont'd),
Lines 45 and 55, change "sheath" to -- combination --.

Signed and Sealed this

Twenty-first Day of March, 2006

JON W. DUDAS
*Director of the United States Patent and Trademark Office*